(12) United States Patent
Dheda et al.

(10) Patent No.: US 12,097,217 B2
(45) Date of Patent: Sep. 24, 2024

(54) MATURATION OF DENDRITIC CELLS

(71) Applicant: Bioclones Proprietary Limited, Cape Town (ZA)

(72) Inventors: Keertan Unkha Jairam Dheda, Cape Town (ZA); Michele Tomasicchio, Cape Town (ZA)

(73) Assignee: BIOCLONES PROPRIETARY LIMITED, Cape Town (ZA)

( * ) Notice: Subject to any disclaimer, the term of this patent is extended or adjusted under 35 U.S.C. 154(b) by 176 days.

(21) Appl. No.: 16/631,099

(22) PCT Filed: Jul. 13, 2018

(86) PCT No.: PCT/IB2018/055192
§ 371 (c)(1),
(2) Date: Jan. 14, 2020

(87) PCT Pub. No.: WO2019/012492
PCT Pub. Date: Jan. 17, 2019

(65) Prior Publication Data
US 2020/0147132 A1 May 14, 2020

(30) Foreign Application Priority Data
Jul. 14, 2017 (GB) .................................... 1711379

(51) Int. Cl.
*A61K 35/15* (2015.01)
*A61K 39/00* (2006.01)
*A61P 37/04* (2006.01)
*C12N 5/0784* (2010.01)

(52) U.S. Cl.
CPC .............. *A61K 35/15* (2013.01); *A61P 37/04* (2018.01); *C12N 5/0639* (2013.01); *A61K 2039/5154* (2013.01); *C12N 2501/2301* (2013.01); *C12N 2501/24* (2013.01); *C12N 2501/52* (2013.01); *C12N 2501/65* (2013.01); *C12N 2506/115* (2013.01)

(58) Field of Classification Search
None
See application file for complete search history.

(56) References Cited

U.S. PATENT DOCUMENTS

2012/0328662 A1   12/2012   Karlsson-Parra et al.

FOREIGN PATENT DOCUMENTS

| WO | WO-2007/110240 A1 | 10/2007 |
| WO | WO-2010/049152 A1 | 5/2010 |
| WO | WO-2014/136845 A1 | 9/2014 |
| WO | WO-2019/012492 A1 | 1/2019 |

OTHER PUBLICATIONS

Jabara et al., 2001, J. Clin. Invest. vol. 107: 371-378.*
Napolitani et al., 2005, Nat. Immunol. vol. 6: 769-776.*
Levy et al., 2006, Blood. vol. 108: 1284-1290.*
Ghosh et al., 2007, Int. Immunoph. vol. 7: 1111-1121.*
Mitchell, 2016, Exp. Rev. Clin. Pharm. vol. 9: 755-770.*
Thumann, 2003, J. Immunol. Methods. vol. 277: 1-16.*
Nguyen-Pham, 2011, Cell. Mole. Immunol. vol. 8: 341-347.*
Banchereau, J. et al. (1998). "Dendritic cells and the control of immunity." *Nature* 392: 245-252.
Boullart, A.C. et al. (2008, e-published Mar. 6, 2008) "Maturation of monocyte-derived dendritic cells with Toll-like receptor 3 and 7/8 ligands combined with prostaglandin $E_2$ results in high interleukin-12 production and cell migration." *Cancer Immunology Immunotherapy* 57(11):1589-1597.
Curtsinger, J.M. et al. (1999). "Inflammatory Cytokines Provide a Third Signal for Activation of Naive $CD4^+$ and $CD8^+$ T cells." *J Immunol* 162: 3256-3262.
Hansen, M. et al. (2013, e-published Nov. 29, 2012). "Comparison of clinical grade type 1 polarized and standard matured dendritic cells for cancer immunotherapy." *Vaccine* 31:639-646.
Hayes, M.P. (1995). "Regulation of Interleukin-12 Expression in Human Monocytes: Selective Priming by Interferon-y of Lipopolysaccharide-Inducible p35 and p40 Genes." *Blood* 86(2)(Jul. 15), 1995: 646-650.
Huang, X-L. et al. (Jun. 2008) "Maturation of dendritic cells for enhanced activation of anti-HIV-1 CD8+ T cell immunity," *Journal of Leukocyte Biology* 83(6):1530-1540.
International Search Report issued in International Application No. PCT/IB2018/055192, mailed Sep. 17, 2018. 5 pages.
Jasani, B. et al. (2009, e-published Feb. 5, 2009). "Ampligen: A potential toll-like 3 receptor adjuvant for immunotherapy of cancer," *Vaccine* 27:3401-3404.
Kristensen, V.N. et al. (Feb. 21, 2012). "Integrated molecular profiles of invasive breast tumours and ductal carcinoma in situ (DCIS) reveal differential vascular and interleukin signaling." *Proc Natl Acad Sci*, USA, 109(8):2802-2807.
Mellman, I. et al. (Aug. 10, 2001). "Dendritic Cells: Specialized and Regulated Antigen Processing Machines." *Cell* 106:255-258.
Mosca, P.J. et al. (2000). "A subset of human monocyte-derived dendritic cells expresses high levels of interleukin-12 in response to combined CD40 ligand and interferon-y treatment." *Blood* 96:3499-3504.
Schmidt, C.S. et al. (1999). "Adjuvant Effect of IL-12: Conversion of Peptide Antigen Administration from Tolerizing to Immunizing for $CD8^+$ T cells In Vivo." *J Immunol* 163: 2561-2567.
Snijders, A. et al. (1998). "High-level IL-12 production by human dendritic cells requires two signals." *Int Immunol* 10(11):1593-1598.

(Continued)

*Primary Examiner* — Amy E Juedes
(74) *Attorney, Agent, or Firm* — Mintz, Levin, Cohn, Ferris, Glovsky and Popeo, P.C.

(57) ABSTRACT

The present invention relates to in vitro methods of producing mature dendritic cells, a dendritic cell maturation cocktail, a method of producing mature antigen presenting dendritic cells in vitro, methods of manufacturing vaccines containing mature dendritic cells, antigen-presenting mature dendritic cells produced according to the methods described, vaccines containing the mature antigen-presenting dendritic cells and methods of treatment and used of mature antigen-presenting cells of the invention.

14 Claims, 10 Drawing Sheets

(56) References Cited

OTHER PUBLICATIONS

Subklewe, M. et al. (2014, e-published Sep. 4, 2014). "New generation dendritic cell vaccine for immunotherapy of acute myeloid leukemia." *Cancer Immunol Immunother* (63):1093-1103.
Written Opinion issued in International Application No. PCT/IB2018/055192, mailed Sep. 17, 2018. 7 pages.
Xiao, Z. et al. (2009). "Programming for CD8 T Cell Memory Development Requires IL-12 or Type I IFN." *J Immunol* 182: 2786-2794.
Zobywalski, A. et al. (Apr. 12, 2007). "Generation of clinical grade dendritic cells with capacity to produce biologically active IL-12p70." *Journal of Translational Medicine BioMed Central* 5(1). 16 pages.

\* cited by examiner

MATURATION OF DENDRITIC CELLS

CROSS-REFERENCE TO RELATED APPLICATIONS

This application is a national stage application filed under 35 U.S.C. § 371, of International Patent Application No. PCT/IB2018/055192, filed Jul. 13, 2018, which claims priority to GB Application No. 1711379.6, filed Jul. 14, 2017, the entire contents of which are incorporated herein by reference in their entirety.

BACKGROUND OF THE INVENTION

Dendritic cells (DCs) are potent antigen presenting cells that link the innate and acquired immune systems. As potent stimulators of B, T lymphocytes and NK cells, they are pivotal to the inception, specificity and regulation of the immune response (Banchereau and Steinman (1998)). In peripheral tissues, they are found in an immature state that is primed towards the uptake, processing and presentation of antigens. Once an antigen is encountered and processed, the dendritic cells undergo a dramatic transformation into a mature cell. During this process, the antigen is presented to other immune function cells that elicit an immune response. Specifically, mature dendritic cells migrate towards the draining secondary lymphoid organs where they interact with T-cells, B-cells and NK cells (Mellman and Steinman (2001)). The applicant has shown that it is possible to harness the antigen presentation abilities of dendritic cells in order to target and eradicate cancers and other infectious diseases in vivo.

The applicant has developed a dendritic cell vaccine against cancer and infectious diseases. In the present invention, a method to mature the dendritic cells (DCs) ex vivo using a dendritic cell maturation cocktail comprising a Toll-like receptor (TLR)-3 agonist (Ampligen), interleukin (IL)-1β (IL-1β), interferons (IFN)-α, IFN-γ, CD40L and a TLR-7/8 agonist (R848) is described for use as an immunotherapeutic intervention against cancer and infectious diseases. While the use of dendritic cells as a vaccine against cancer is not a new therapy, the specific combination of maturation agents has not been previously described.

The applicant has in vitro pre-clinical evidence that its dendritic cell vaccine is tumoricidal against cancer cells. Dendritic cells matured with the maturation cocktail of the invention displayed an optimal maturation phenotype which could polarize an anti-tumour T-helper response against cancer cells. The applicant further presents evidence that these mature dendritic cells produced high levels of the Th1 effector cytokines, IFN-γ and IL-12p70 which are an indicator of the capability of a dendritic cell vaccine to activate and prime an anti-tumour Th1 CD8+ T-cell response in vivo (Curtsinger et al. (1999), Schmidt and Mescher (1999), Xiao et al. (2009)). Furthermore, IL-12p70 has been shown to be indispensable in regulating CD8+ effector function, T-cell activation and has been shown to be a key indicator in more favourable clinical outcomes amongst breast cancer patients (Curtsinger et al. (1999), Schmidt and Mescher (1999), Xiao et al. (2009), Kristensen et al. (2012)).

The major advantage of the current invention is that the applicant has developed a model maturation method and maturation cocktail that can be readily applied to other types of cancers and infectious diseases. The maturation cocktail could be used in conjunction with an antigen from the cancer or infectious disease the investigator wishes to target. The current technology is safe and directly transferable to other diseases.

SUMMARY OF THE INVENTION

In a first aspect of the invention there is provided for an in vitro method of producing mature dendritic cells, the method comprising the step of (i) culturing immature dendritic cells in the presence of a Toll-like receptor-3 (TLR-3) agonist, IFN-α, IFN-γ, CD40L, IL-1β and a Toll-like receptor-7/8 (TLR-7/8) agonist.

In one embodiment of the invention the TLR-3 agonist is Ampligen® (ritatolimod) and the TLR-7/8 agonist is R848. The TLR-3 agonist may also be a high molecular weight dsRNA polymer selected from the group consisting of poly [I]:poly [CxU]; poly [I]:poly [GxU]; poly [A]:poly [UxC]; poly [A]:poly [UxG]; poly [U]:poly [AxC]; poly [U]:poly [IxU]; poly [C]:poly [GxA]; poly [C]:poly [GxU]; poly [G]:poly [CxA]; and poly [G]:poly [CxU], where x is on average a number from 3 to 40, preferably a number from 6 to 20. More preferably the dsRNA polymer may be selected from the group consisting of poly [I]:poly [C12U] and poly [C]:poly [I12U].

In a second embodiment of the invention the immature dendritic cells are cultured from a sample of peripheral blood mononuclear cells. It will be appreciated that the sample is isolated from a human or animal.

In a third embodiment of the invention the dendritic cells are cultured in the presence of an antigen. In a preferred embodiment the antigen is a cancer antigen or an infectious disease antigen.

It will be appreciated that a cancer may be selected from the group consisting of adrenal cancer including adrenocortical carcinoma and pheochromocytoma; anal cancer; appendix cancer; bile duct cancer including cholangiocarcinoma, extrahepatic bile duct cancer and intrahepatic bile duct cancer; bladder cancer including ureteral cancer, bone cancer including chondrosarcoma, Ewing sarcoma, osteogenic sarcoma, osteosarcoma, mesenchymal chondrosarcoma and bone sarcoma; brain cancer including anaplastic astrocytoma, astrocytoma, brain stem glioma, brain tumour, craniopharyngloma, diffuse astrocytoma, ependymoma, germ cell tumour, gliloblastoma multiforme, glioma, low-grade astrocytoma, medulloblastoma, meningloma, mixed gliomas, ollgodendroglloma, peripheral nerve cancer, pilocytic astrocytoma, pineal region tumour and pituitary gland cancer; breast cancer including ductal carcinoma in situ, male breast cancer, medullary carcinoma, infiltrating ductal carcinoma, infiltrating lobular carcinoma, inflammatory breast cancer, Invasive or Infiltrating breast cancer, lobular carcinoma in situ, metastatic breast cancer, mucinous carcinoma, Paget's disease, papillary carcinoma, triple-negative breast cancer and tubular carcinoma; cervical cancer; colorectal cancer including bowel cancer, colon cancer and rectal cancer; oesophageal cancer; eye cancer; gallbladder cancer; gastrointestinal cancer including gastrointestinal carcinoid cancer and gastrointestinal stromal tumours; head and neck cancer including neck cancer, tonsil cancer and metastatic squamous neck cancer; hemangioendothelioma; Hodgkin lymphoma including Hodgkin's disease; intestinal cancer; kidney cancer including renal cell carcinoma, renal pelvis cancer and ureteral cancer; leptomeningeal metastases; leukaemia including acute granulocytic leukaemia, acute lymphocytic leukaemia, acute myelogenous leukaemia, chronic lymphocytic leukaemia, chronic myelogenous leukaemia, hairy cell leukaemia and myelodysplastic syndrome; liver cancer; lung cancer including adenocarcinoma, adenosarcoma, small cell lung cancer, non-small cel lung cancer and oat cell cancer; melanoma including cutaneous melanoma and metastatic melanoma; mesothelioma; multiple myeloma including bone marrow cancer; neuroblastoma; neuroendocine tumours; Non-Hodgkin lymphoma (NHL) including B-Cell lymphoma, lymph node cancer, lymphoma, mycosis fungoldes and T-cell lymphoma; ocular cancer; ocular melanoma; oral cancer including lip cancer, oral cavity cancer, jaw cancer, kaposi sarcoma, mouth cancer, mucosal melanoma, salivary gland cancer and tongue cancer; ovarian cancer including fallopian tube cancer, ovarian epithelial cancer, ovarian germ cell tumour, ovarian primary peritoneal carcinoma, ovarian sex cord stromal tumour and peritoneal cancer; pancreatic cancer including islet cell cancer; paranasal sinus cancer; pelvic cancer; penile cancer; primary central nervous system lymphoma; prostate cancer; soft tissue sarcoma including fibrosarcoma and synovial sarcoma; sinus cancer; skin cancer including basal cell carcinoma, cutaneous lymphoma, squamous cell carcinoma and Merkel cell carcinoma; small intestine cancer; soft tissue sarcoma including angiosarcoma, epithelioid sarcoma, liposarcoma; lelomyosarcoma and rhabdomyosarcoma; spinal cancer including spinal column cancer, spinal cord cancer and spinal tumour; stomach cancer including carcinoid tumours and gastric cancer, testicular cancer; throat cancer including hypopharyngeal cancer, laryngeal cancer, nasal cavity cancer, nasopharyngeal cancer, oropharyngeal cancer and pharyngeal cancer, thymoma or thymic carcinoma; thyroid cancer including parathyroid cancer; tubal cancer; urethral cancer; uterine cancer including endometrial cancer, uterine adenocarcinoma, uterine sarcoma and uterine sarcoma; vaginal cancer and vulvar cancer.

It will further be appreciated that the infectious disease may be selected from the group consisting of a viral infection, a parasitic infection, a fungal infection or a bacterial infection. Preferably, the infectious disease is selected from the group consisting of tuberculosis, HIV-1, malaria, ebola virus and influenza.

In a second aspect of the invention there is provided for a dendritic cell maturation cocktail, comprising a TLR-3 agonist, IFN-α, IFN-γ, CDL40, IL-1β and a TLR-7/8 agonist.

In one embodiment of the invention the TLR-3 agonist is Ampligen® (rintatollmod) and the TLR-7/8 agonist is R848. The TLR-3 agonist may also be a high molecular weight dsRNA polymer selected from the group consisting of poly [I]:poly [CxU]; poly [I]:poly [GxU]; poly [A]:poly [UxC]; poly [A]:poly [UxG]; poly [U]:poly [AxC]; poly [U]:poly [IxU]; poly [C]:poly [GxA]; poly [C]:poly [GxU]; poly [G]:poly [CxA]; and poly [G]:poly [CxU], where x is an integer from 3 to 40, preferably a number from 6 to 20. More preferably the dsRNA polymer may be selected from the group consisting of poly [I]:poly [C12U] and poly [C]:poly [I12U].

In yet a further embodiment of the invention the dendritic cell maturation cocktail is used for the in vitro maturation of an immature dendritic cell in the presence of an antigen. In a preferred embodiment the antigen is a cancer antigen or an infectious disease antigen.

In a third aspect of the invention there is provided for a method of producing mature antigen-presenting dendritic cells in vitro, the method including the steps of (i) exposing an immature dendritic cell to an antigen, and (ii) maturing the dendritic cell according to the methods described herein or with the dendritic cell maturation cocktail described herein.

In one embodiment of the invention the antigen is a cancer antigen or an infectious disease antigen.

In yet a further embodiment of the invention the immature dendritic cell is exposed to the antigen for sufficient time to induce the immature dendritic cell to capture and process the antigen.

In a fourth aspect of the invention there is provided for a method of manufacturing a vaccine for inducing a cellular immune response in a subject, wherein the method comprises the steps of (i) exposing an immature dendritic cell to an antigen in vitro, (II) maturing the immature dendritic cell with the dendritic cell maturation cocktail until a sufficient number of the dendritic cells become antigen-presenting mature dendritic cells, and (iii) formulating the antigen-presenting mature dendritic cells in a pharmaceutically acceptable formulation.

In another embodiment of the invention the antigen is a cancer antigen or an infectious disease antigen.

In a fifth aspect of the invention there is provided for an antigen-presenting mature dendritic cell produced with the dendritic cell maturation cocktail described herein and/or according to the methods described herein.

In a sixth aspect of the invention there is provided for a vaccine which includes antigen-presenting mature dendritic cells produced with the dendritic cell maturation cocktail described herein and/or produced by the methods described herein.

In one embodiment the vaccine may further include a suitable diluent, excipient or adjuvant.

In a seventh aspect of the invention there is provided for the vaccine of the present invention or the antigen-presenting mature dendritic cell of the present invention for use in a method of inducing an immune response to a cancer or an infectious disease in a subject, the method comprising administering an immunogenically effective amount of the vaccine to the subject.

In an eighth aspect of the invention there is provided for a method of inducing an immune response to a cancer or an infectious disease in a subject, the method comprising administering an immunogenically effective amount of the vaccine described herein or the antigen-presenting mature dendritic cell of the present invention to the subject.

BRIEF DESCRIPTION OF THE FIGURES

Non-limiting embodiments of the invention will now be described by way of example only and with reference to the following figures.

Immature dendritic cells were differentiated from monocytes. The iDCs were then matured in CellGro medium with or without 100 μg/mL Ampligen® and 10 ng/mL IL-11 (Amp+IL-1β), 2.5 μg/mL R848 and 10 ng/mL IL-1β (R848+IL-1β), an IFN-containing cocktail (10 ng/mL IFN-α, 25 ng/mL IFN-α, 1 μg/mL CD40L and 10 ng/mL IL-1β), 100 μg/mL Ampligen® and IFN-containing cocktail (Amp+IFN-cocktail), or 100 μg/mL Ampligen®, IFN-containing cocktail and 2.5 μg/mL R848 (Amp+IFN-cocktail+R848) for 48 hrs at 37° C. The monocytes, immature dendritic cells and mature dendritic cells were subjected to a haematoxylin and eosin (HE) stain or were stained with CD14 PE-CY7 (monocytes), CD40 FITC (immature and mature DCs) and or CD83 APC (mature DCs; A) for confocal microscopy. The maturation phenotype was also determined by flow cytometry (B). The histogram shows pooled results from two independent experiments and samples from four donors. Statistical significance was determined by one-way ANOVA with Dunnett's post-test, where *, , * indicates $p<0.05$, $p<0.01$, or $p<0.001$, respectively. Error bars represent standard deviation. Light microscopy magnification: 100× (oil immersion); scale bars=20 μm. Confocal magnification: 63× (oil immersion); scale bars=10 μm.

Figure 3:
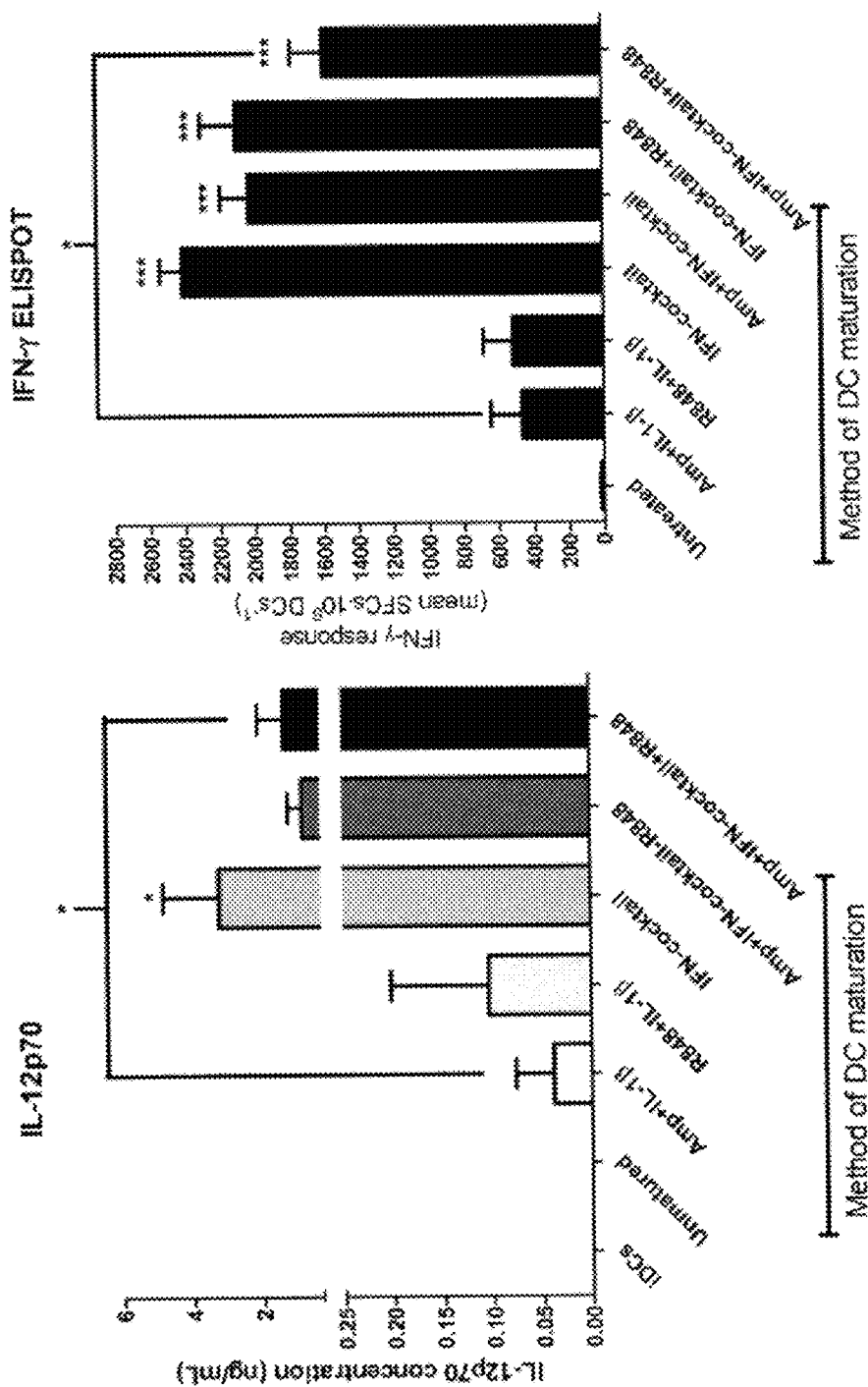

FIG. 3: Dendritic cells matured with Ampligen®, an IFN-containing cocktail and R848 express higher levels of the Th1 effector cytokines, IL-12p70 and IFN-γ, compared to dendritic cells matured with Ampligen® or R848 and IL-1β alone. Dendritic cells were differentiated from monocytes and matured as indicated previously. (A) The levels of IL-12p70 from the supernatants were determined using the ELIZAPRO IL-12p70 detection kit from Mabtech as indicated by the manufacturer. (B) For the IFN-γ ELISPOT assay IDCs were plated at $2\times10^5$, $1\times10^5$ or $0.5\times10^5$ cell per well in a 96-well ELISPOT plate and matured as indicated for 48 hrs at 37° C. The cells were washed and the plate was processed as indicated by the manufacturer (Mabtech). The histogram shows pooled results from four donors. Statistical significance was determined by one-way ANOVA with Dunnett's post-test, where *, *** Indicates $p<0.05$ or $p<0.001$, respectively. Error bars represent standard deviation. IDCs=Immature DCs, Amp=Ampligen®, IFN-containing cocktail=IFN-γ, IFN-γ, CD40L and IL-1β. Note: for the IFN-γ ELISPOT assay recombinant IFN-γ was excluded from the IFN-containing cocktail.

Figure 4:
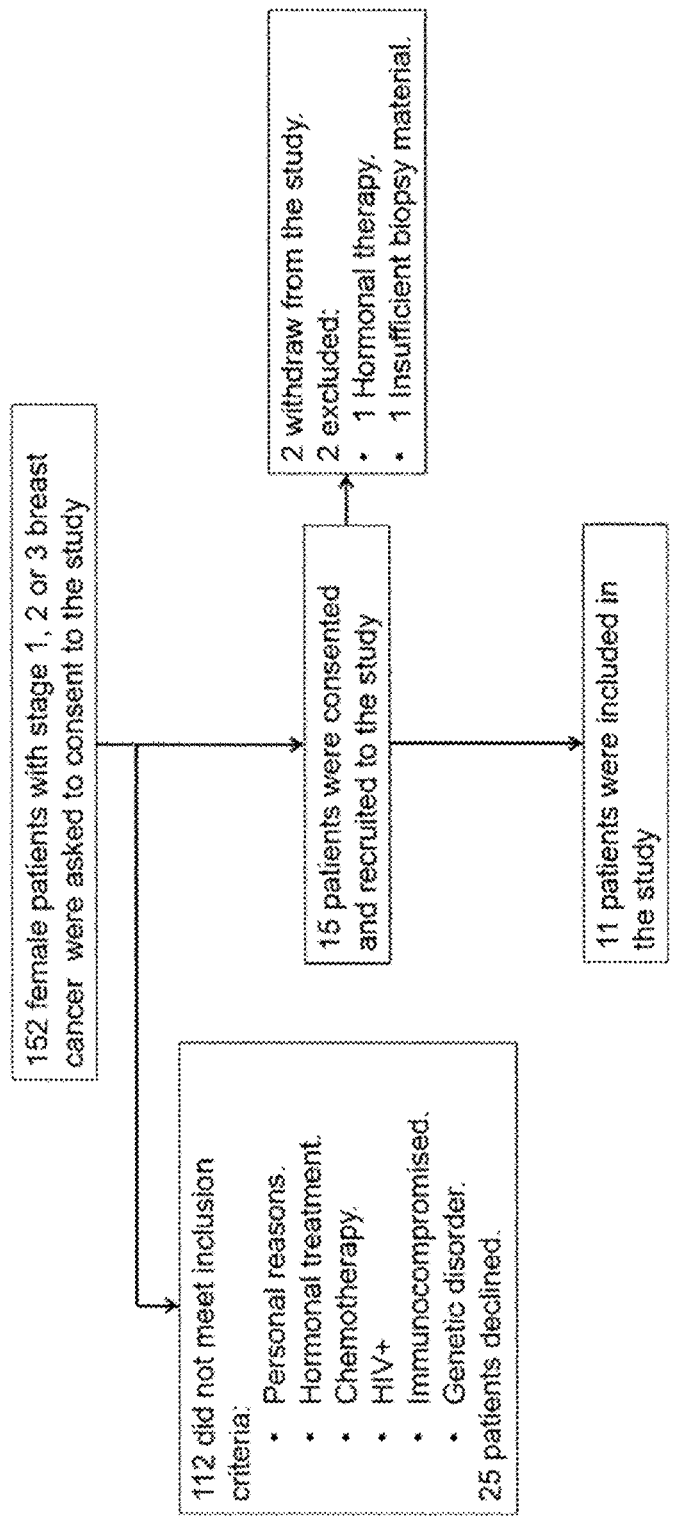

FIG. 4: Patient recruitment plan for the preclinical trial.

Figure 5:
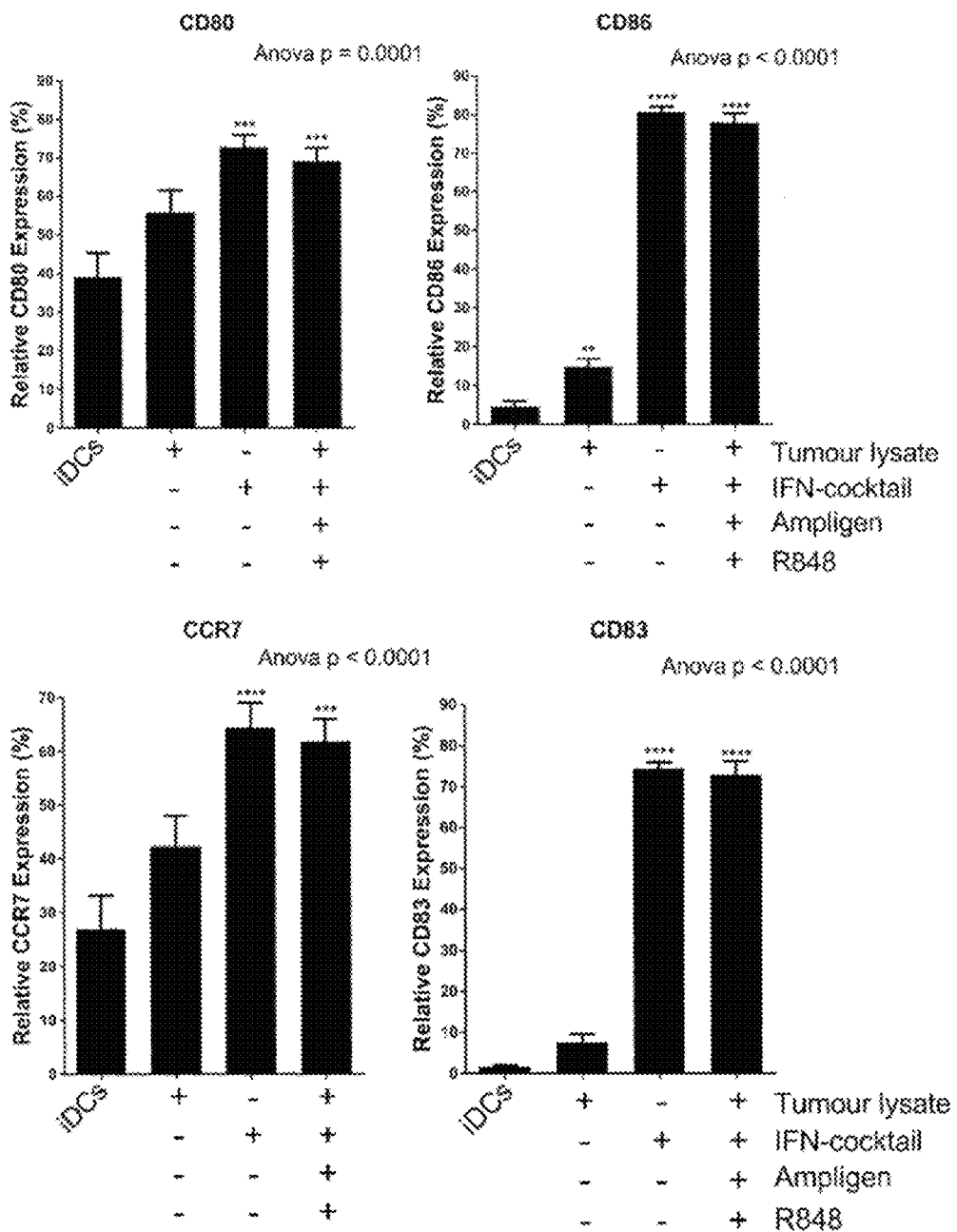

FIG. 5: Dendritic cells, from patients with breast cancer, matured with Ampligen®, an IFN-containing cocktail, R848 and tumour-specific lysate or with IFN-cocktail only express higher levels of co-stimulatory molecules compared to iDCs or dendritic cells matured with tumour-specific lysate only. Immature dendritic cells were differentiated from monocytes, Incubated in CellGro medium with or without 100 μg/mL tumour-specific lysate for 6 hrs at 37° C. The cells were then matured with or without, an IFN-containing cocktail only (10 ng/mL IFN-α, 25 ng/mL IFN-γ, 1 μg/mL CD40L and 10 ng/mL IL-11), or 100 μg/mL Ampligen®, an IFN-containing cocktail and 2.5 μg/mL R848 (Amp+IFN-cocktail+R848) for 42 hrs at 37° C. The maturation phenotype was determined by flow cytometry. Statistical significance was determined by one-way ANOVA with Dunnett's post-test, where *, , * indicates $p<0.05$, $p<0.01$, or $p<0.005$, respectively. Error bars represent standard deviation.

Figure 6:
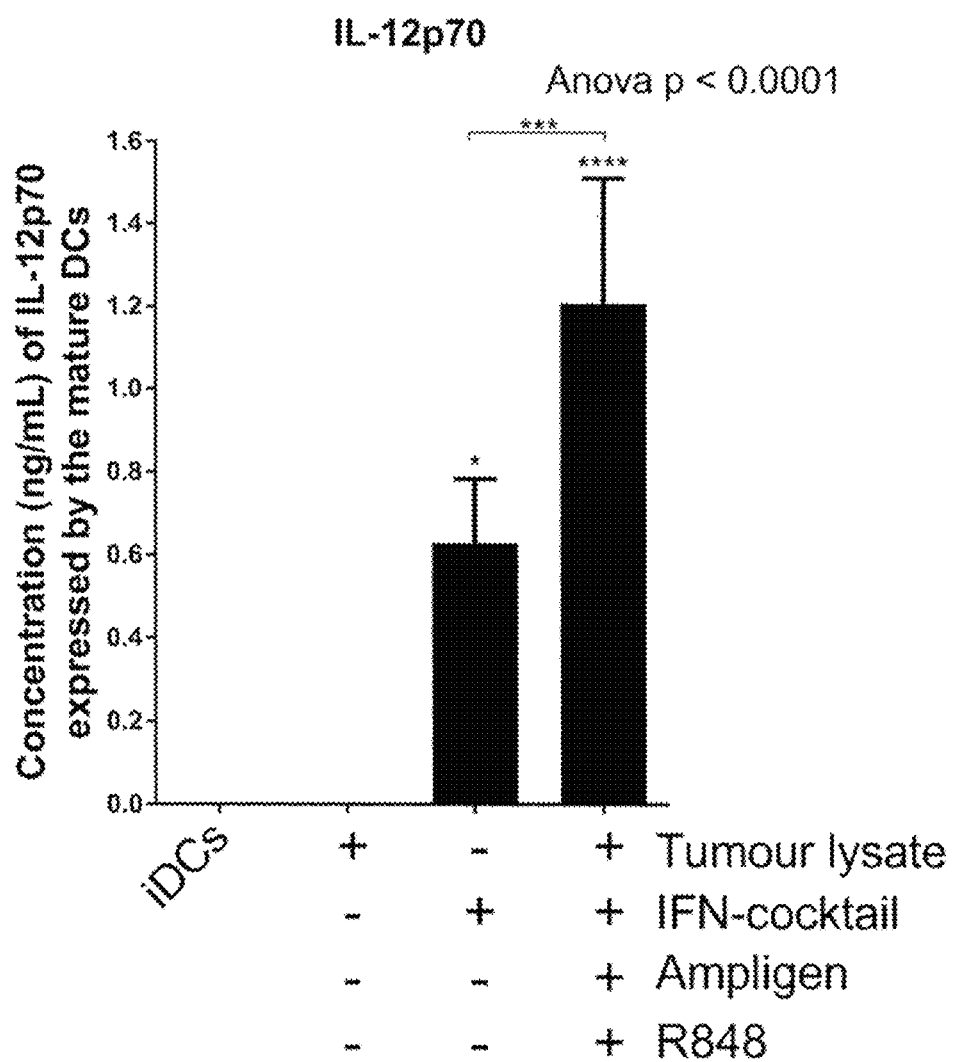

FIG. 6: Dendritic cells matured with Ampligen®, an IFN-cocktail (IFN-α, IFN-γ, CD40L and IL-1β), R848 and tumour-specific lysate express higher levels of the Th1 effector cytokines, IL-12p70 compared to the immature dendritic cells (iDCs) or dendritic cells matured with tumour-specific lysate only (Lysate only) or with IFN-containing cocktail only. The level of IL-12p70 from the supernatants of the immature dendritic cells or matured dendritic cells was determined using the ELIZAPRO IL-12p70 detection kit from Mabtech as indicated by the manufacturer. The histogram shows pooled results from four donors. Statistical significance was determined by one-way ANOVA with Dunnett's post-test or a Wilcoxon rank sum paired t test, where *, *** indicates $p<0.05$ or $p<0.001$, respectively. Error bars represent standard deviation.

Figure 7:
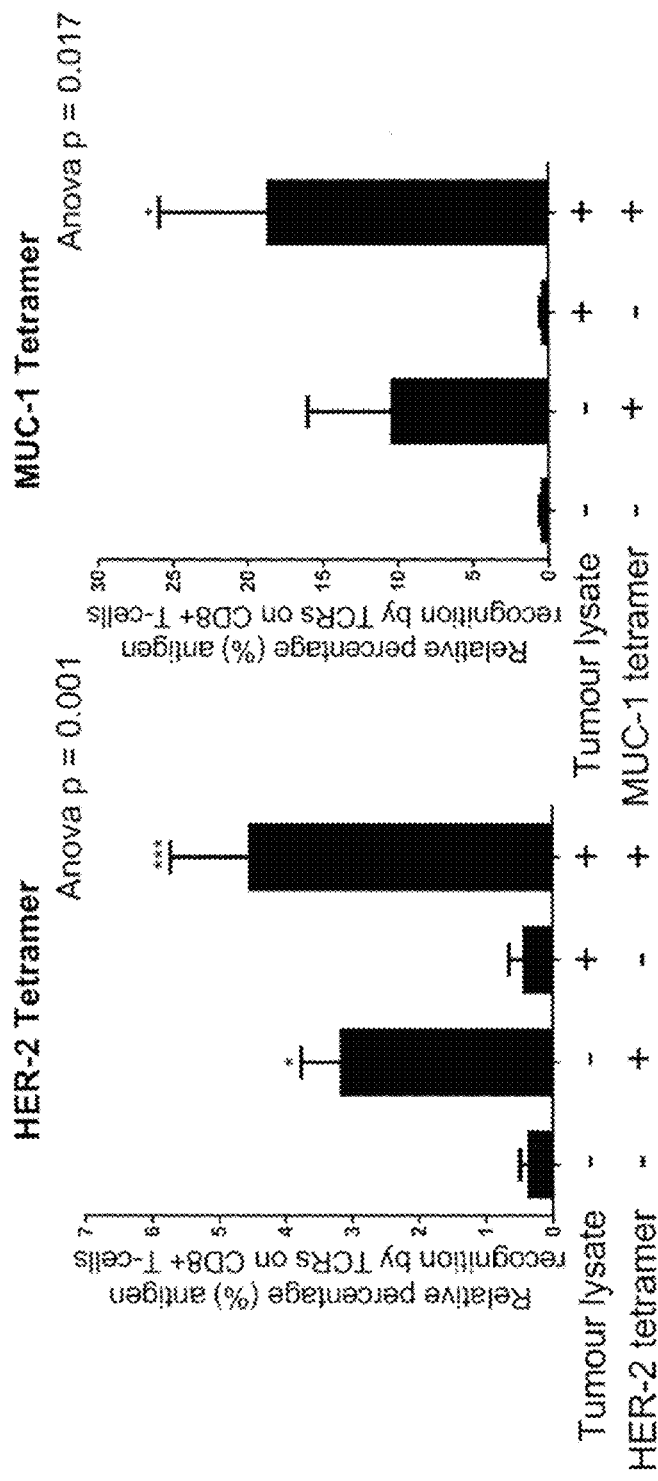

FIG. 7: The tumour-specific dendritic cell-primed CD8+ T-cells can recognise HER-2 and MUC-1 antigens by their T-cell receptors. Effector cells were generated and antigens recognised by TCRs of CD8+ T-cells were determined by staining with CD8 FITC, CD3 PerCP/Cy5.5, HER-2 APC tetramer, and MUC-1 PE tetramer as indicated by the manufacturer. The levels of antigen presentation were determined by flow cytometry. Histogram A shows pooled results from three individual experiments with three donors, while histogram B shows pooled results from two individual experiments with two donors. Statistical significance was determined by one-way ANOVA with Dunnett's post-test, where *, *** indicates $p<0.05$ or $p<0.005$, respectively. Error bars represent standard deviation.

Figure 8:
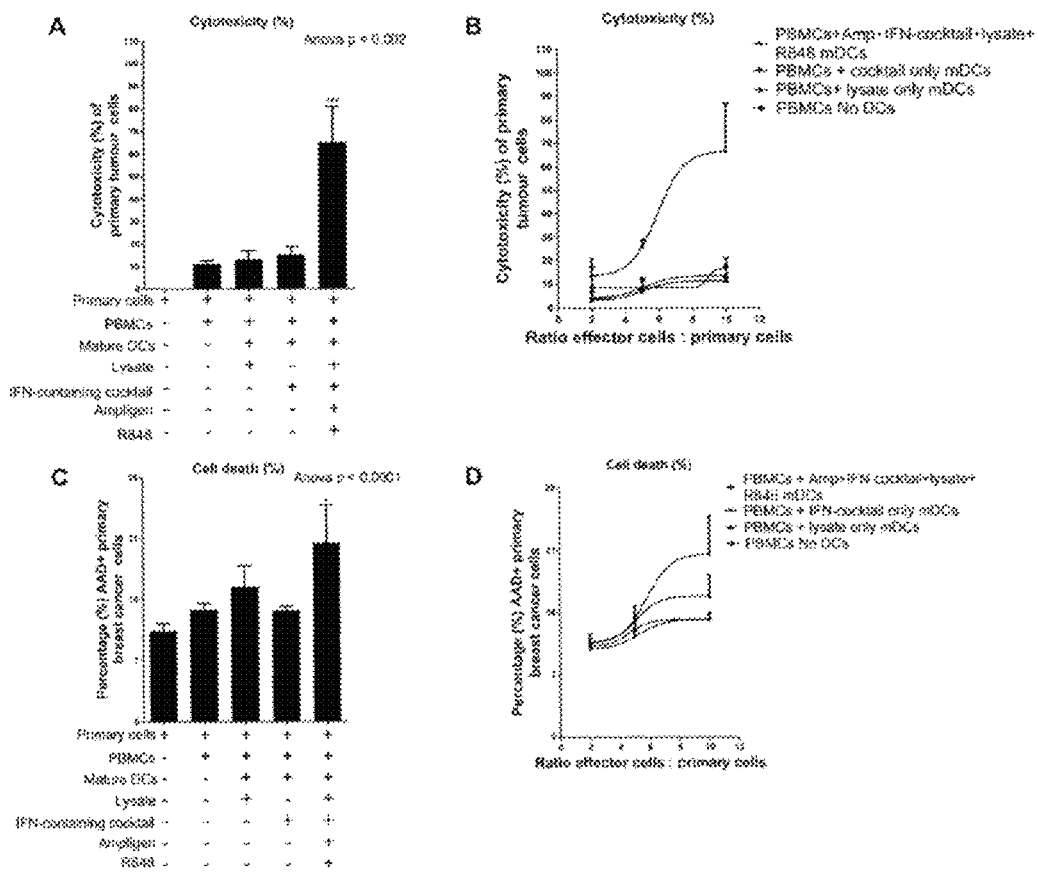

FIG. 8: PBMCs from stage 1, 2 and 3 breast cancer patients co-cultured ex vivo with Ampligen®, an IFN-cocktail, R848 and tumour-specific lysate-matured dendritic cells results in cytotoxic T-lymphocyte-mediated killing of primary breast cancer cells in vitro. Matured dendritic cells were prepared as indicated in figure legend 2. The matured dendritic cells were then co-cultured with PBMC at a ratio of 1:10 for 7 days at 37° C. The primary breast cancer cells were incubated with or without (no PBMCs) the primed PBMCs (effector cells) at a ratio of 1:10 or the primary cells were incubated with the effector T-cells at various ratios for 4 hrs at 37° C. Cytotoxicity (A and B) was determined using the LDH assay (Cytotoxicity Detection KtPlus LDH; Roche, Germany) and cell death (C and D) of the primary breast cancer cells was measured by flow cytometry using the apoptosis detection kit from Becton Dickinson. Error bars represent standard deviation.

Figure 9:
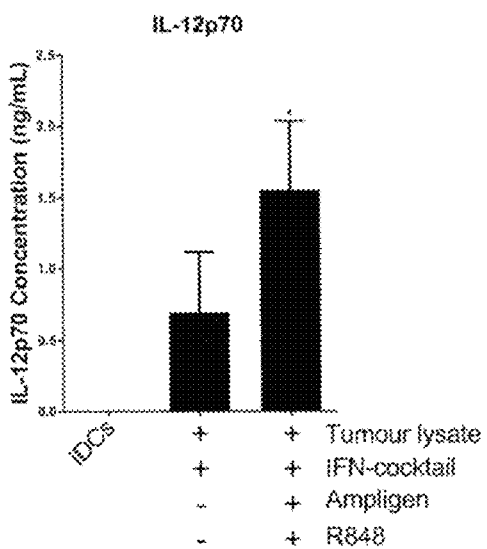

FIG. 9: Dendritic cells matured with the maturation method disclosed in this specification have a higher efficacy than those described in WO02014136845A1, as assessed by IL12p70 expression. Immature dendritic cells were prepared as indicated previously. The immature dendritic cells were loaded with 100 μg/ml of MCF-7 lysate. After 6 hrs incubation at 37° C. the cells were matured with an IFN-containing cocktail or Ampligen®, an IFN-containing cocktail and R848 for 42 hrs at 37° C. The level of IL-12p70 from the supernatants of the immature dendritic cells or matured dendritic cells were determined using the ELIZAPRO IL-12p70 detection kit from Mabtech (USA) as indicated by the manufacturer. Statistical significance was measured using Anova with a Dunnetts post-test, where * represents $p<0.05$. Error bars represent standard deviation.

Figure 10:
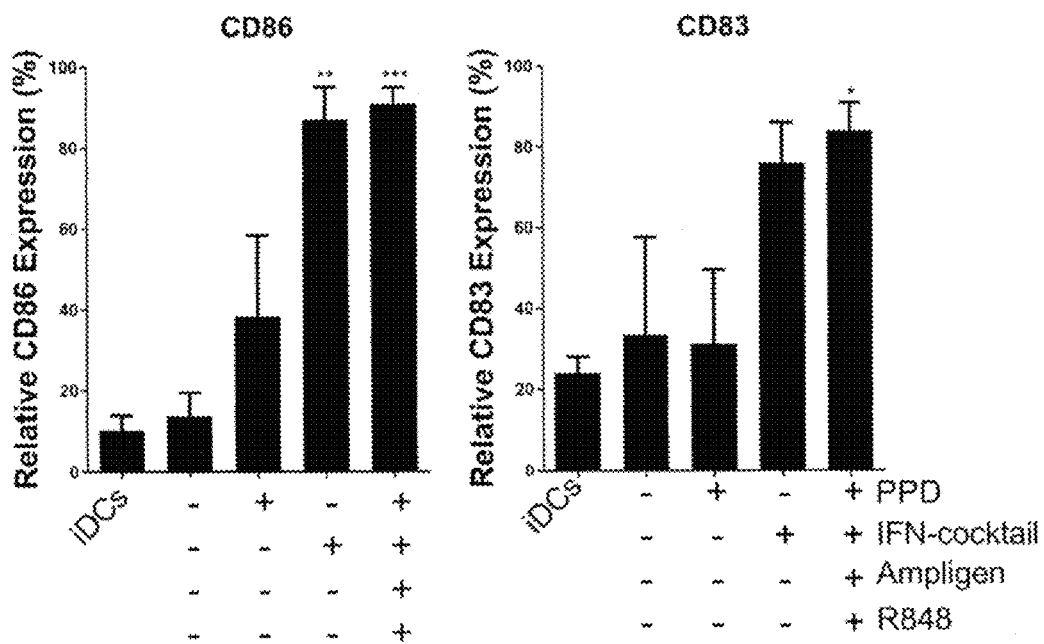

FIG. 10: Dendritic cells matured with PPD, Ampligen, an IFN-cocktail and R848 or IFN-cocktail alone produce high levels of the maturation markers CD86 and CD83. The mature dendritic cells were prepared as indicated in the text and the maturation phenotype was determined by flow cytometry. The histogram shows pooled results from three independent experiments and samples from three donors. Error bars represent standard deviation.

Figure 11:
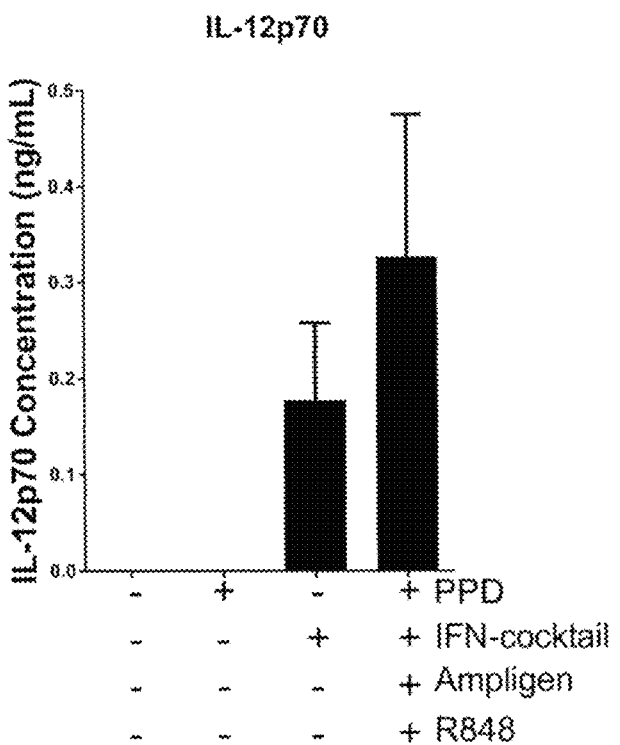

FIG. 11: Dendritic cells primed and matured with PPD and the full cocktail produce high levels of the Th1 effector cytokine IL-12p70. The levels of IL-17p70 were determined from the culture supernatants of the matured dendritic cells using the IL-12p70 ELISAPRO detection kit according to the manufacturers specifications (Mabtech, USA). The histogram shows pooled results from three independent experiments and samples from three donors. Error bars represent standard deviation.

Figure 12:
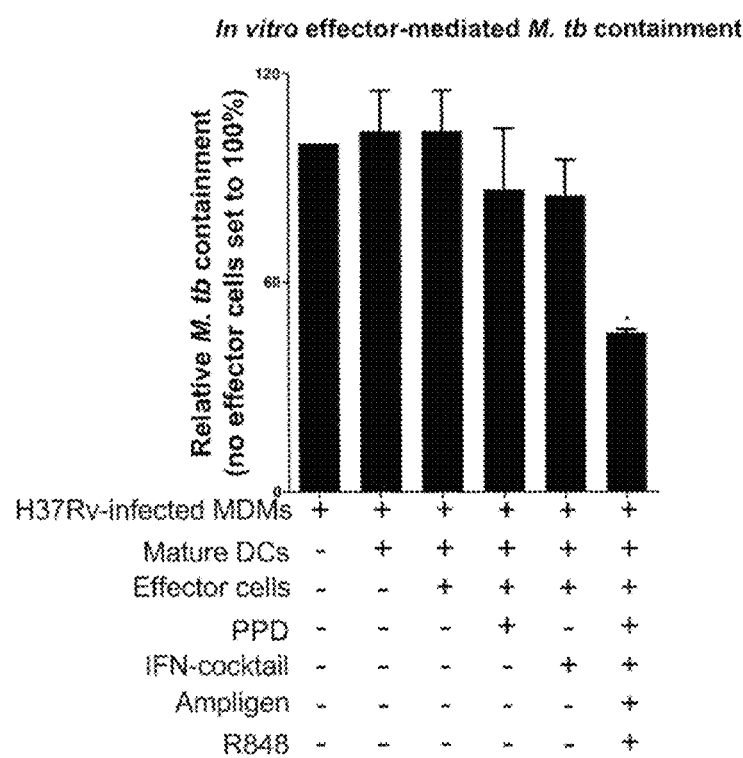

FIG. 12: Dendritic cells matured with the intervention have the ability to prime effector cells resulting in bactericidal containment of *M. tuberculosis* in vitro. Effector cells were primed with or not primed with the mature dendritic cells at 37° C. for 7 days. The effector cells were then co-cultured with *M. tuberculosis* infected MDMs for 24 hrs at 37° C. *M. tuberculosis* containment was then determined by counting CFUs using a standard method. The histogram shows pooled results from three independent experiments and samples from three donors. Error bars represent standard deviation.

DETAILED DESCRIPTION OF THE INVENTION

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" Include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

The present invention relates to a dendritic cell maturation cocktail and methods of using the dendritic cell maturation cocktail in order to prepare mature dendritic cells which present antigens against cancers and infectious diseases.

The technology and methodology described herein will assist with preparation of mature dendritic cells which boost the immune response.

The applicant has shown that the method of the present invention is useful for successfully preparing mature dendritic cells for use as an immunotherapeutic intervention against cancer and other infectious diseases.

The maturation cocktail of the invention has not been previously described and presents a unique combination of maturation agents which have been shown to be more efficacious than other known maturation cocktails.

The maturation cocktail of the invention includes a Toll-like receptor-3 agonist (Ampligen®), interleukin 10 (IL-1β), interferon α (INF-α), Interferon γ (INF-γ) CD40L and a Toll-like receptor 7/8 agonist (R848).

The term "cell culture" refers to maintenance and growth, cultivation, or expansion of cells dissociated from the parent tissue in an artificial environment outside of a hosts body. This can be in an in vitro environment or alternatively an ex vivo environment. The use of the term "cell culture" is generic and can be used interchangeably with the term "tissue culture". Both terms, "cell culture" and "tissue culture," can be used when referring to individual cells, a group of cells, a group or mixture of different or like cell types, tissues, and organs.

The terms "propagation medium", "cell culture medium," "culture medium," or "tissue culture medium" can be used interchangeably and refer to a nutritional solution for cultivating cells, tissues, or organs.

The vaccine or mature dendritic cells of the invention can be provided either alone or in combination with other compounds, in the presence of an adjuvant, or any carrier, such as a pharmaceutically acceptable carrier and in a form suitable for administration to mammals, for example, humans or animals.

As used herein a "pharmaceutically acceptable carrier" or "excipient" includes any and all antibacterial and antifungal agents, coatings, dispersion media, solvents, isotonic and absorption delaying agents, and the like that are physiologically compatible. A "pharmaceutically acceptable carrier" may include a solid or liquid filler, diluent or encapsulating substance which may be safely used for the administration of the mature dendritic cells or vaccine to a subject. The pharmaceutically acceptable carrier can be suitable for aerosol, intracapsular, intracistemal, intracranial, intramuscular, Intranasal, Intraorbital, intraperitoneal, intraspinal, intrathecal, intravenous, Intraventricular, ophthalmic, oral, parenteral, subcutaneous, sublingual or topical administration. Pharmaceutically acceptable carriers include sterile aqueous solutions, dispersions and sterile powders for the preparation of sterile solutions. The use of media and agents for the preparation of pharmaceutically active substances is well known in the art. Where any conventional media or agent is incompatible with the mature dendritic cells, use thereof in the vaccines of the invention is not contemplated. Supplementary active compounds can also be incorporated into the vaccines.

Suitable formulations to administer the antigen-presenting mature dendritic cells or vaccines to subjects who are to be prophylactically treated for a cancer or a infectious disease, who are suffering from a cancer or infectious disease and which are presymptomatic for a condition associated with a cancer or infectious disease fall within the scope of the invention. Any appropriate route of administration may be employed, such as, aerosol, intracapsular, intracistemal, intracranial, intramuscular, intranasal, intraorbital, intraperitoneal, intraspinal, Intrathecal, intravenous, intraventricular, ophthalmic, oral, parenteral, subcutaneous, sublingual or topical administration.

As used herein the term "subject" includes mammals, for example, humans or an animal.

For vaccine formulations, an effective amount of the antigen-presenting mature dendritic cells of the invention can be provided, either alone or in combination with other compounds, with immunological adjuvants, for example, aluminium hydroxide dimethyldioctadecylammonium hydroxide or Freund's incomplete adjuvant. The antigen-presenting mature dendritic cells of the invention may also be linked with suitable carriers and/or other molecules, such as bovine serum albumin or keyhole limpet hemocyanin in order to enhance immunogenicity.

In some embodiments, the antigen-presenting mature dendritic cells or vaccines according to the invention may be provided in a kit, optionally with a carrier and/or an adjuvant, together with instructions for use.

An "effective amount" of the antigen-presenting mature dendritic cells or vaccines according to the invention includes a therapeutically effective amount, immunologically effective amount, or a prophylactically effective amount.

A "therapeutically effective amount" refers to an amount effective, at dosages and for periods of time necessary, to achieve the desired therapeutic result, such as treatment of a cancer or infectious disease or a condition associated with such cancer or infectious disease. The outcome of the treatment may for example be measured by a delay in development of a pathology associated with the cancer or infectious disease, stimulation of the immune system, or any other method of determining a therapeutic benefit. A therapeutically effective amount of the antigen-presenting mature dendritic cells may vary according to factors such as the disease state, age, sex, and weight of the individual, and the ability of the antigen-presenting mature dendritic cell to elicit a desired response in the individual. Dosage regimens may be adjusted to provide the optimum therapeutic response. A therapeutically effective amount is also one in which any toxic or detrimental effects of the antigen-presenting mature dendritic cells are outweighed by the therapeutically beneficial effects.

The dosage of any of the antigen-presenting mature dendritic cells or vaccines of the present invention will vary depending on the symptoms, age and body weight of the subject, the nature and severity of the disorder to be treated or prevented, the route of administration, the disease being treated and the form of the vaccine. Any of the antigen-presenting mature dendritic cells or vaccines of the invention may be administered in a single dose or in multiple doses. The dosages of the antigen-presenting mature dendritic cells or vaccines of the invention may be readily determined by techniques known to those of skill in the art or as taught herein.

By "immunogenically effective amount" is meant an amount effective, at dosages and for periods of time necessary, to achieve a desired immune response. The desired immune response may include stimulation or elicitation of an immune response, for instance a T or B cell response.

A "prophylactically effective amount" refers to an amount effective, at dosages and for periods of time necessary, to achieve a desired prophylactic result, such as prevention of onset of a condition associated with an infectious disease. Typically, a prophylactic dose is used in subjects prior to or at an earlier stage of disease, so that a prophylactically effective amount may be less than a therapeutically effective amount.

Dosage values may vary with the severity of the condition to be alleviated. For any particular subject, specific dosage regimens may be adjusted over time according to the individual need and the judgment of the person administering or supervising the administration of the antigen-presenting mature dendritic cells or vaccines of the invention. Dosage ranges set forth herein are exemplary only and do not limit the dosage ranges that may be selected. The amount of antigen-presenting mature dendritic cells in the vaccines may vary according to factors such as the disease state, age, sex, and weight of the individual. Dosage regimens may be adjusted to provide the optimum therapeutic response. For example, a single dose may be administered, or multiple doses may be administered over time. It may be advantageous to formulate the vaccines in dosage unit forms for ease of administration and uniformity of dosage.

The term "preventing", when used in relation to a cancer or an infectious disease, or other medical disease or condition, is well understood in the art, and includes administration of a composition which reduces the frequency of or delays the onset of symptoms of the condition in a subject relative to a subject which does not receive the composition. Prevention of a disease includes, for example, reducing the number of diagnoses of the cancer or infection in a treated population versus an untreated control population, and/or delaying the onset of symptoms of the cancer or infection in a treated population versus an untreated control population.

The term "prophylactic or therapeutic" treatment is well known to those of skill in the art and includes administration to a subject of one or more of the antigen-presenting mature dendritic cells or vaccines of the invention. If the antigen-presenting mature dendritic cell or vaccine is administered prior to clinical manifestation of an unwanted condition (e.g., disease or other unwanted state of the subject) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

Toxicity and therapeutic efficacy of antigen-presenting mature dendritic cells or vaccines of the invention may be determined by standard pharmaceutical procedures in cell culture or using experimental animals, such as by determining the $LD_{50}$ and the $ED_{50}$. Data obtained from the cell cultures and/or animal studies may be used to formulate a dosage range for use in a subject. The dosage of any antigen-presenting mature dendritic cell or vaccine of the invention lies preferably within a range of circulating concentrations that include the $ED_{50}$ but which has little or no toxicity. The dosage may vary within this range depending upon the dosage form employed and the route of administration utilized. For vaccines of the present invention, the therapeutically effective dose may be estimated initially from cell culture assays.

The following examples are offered by way of illustration and not by way of limitation.

Example 1

Determination of the Optimal Culture Conditions Required to Generate Immature Dendritic Cells (iDC) from Blood-Derived Monocytes.

Figure 1:
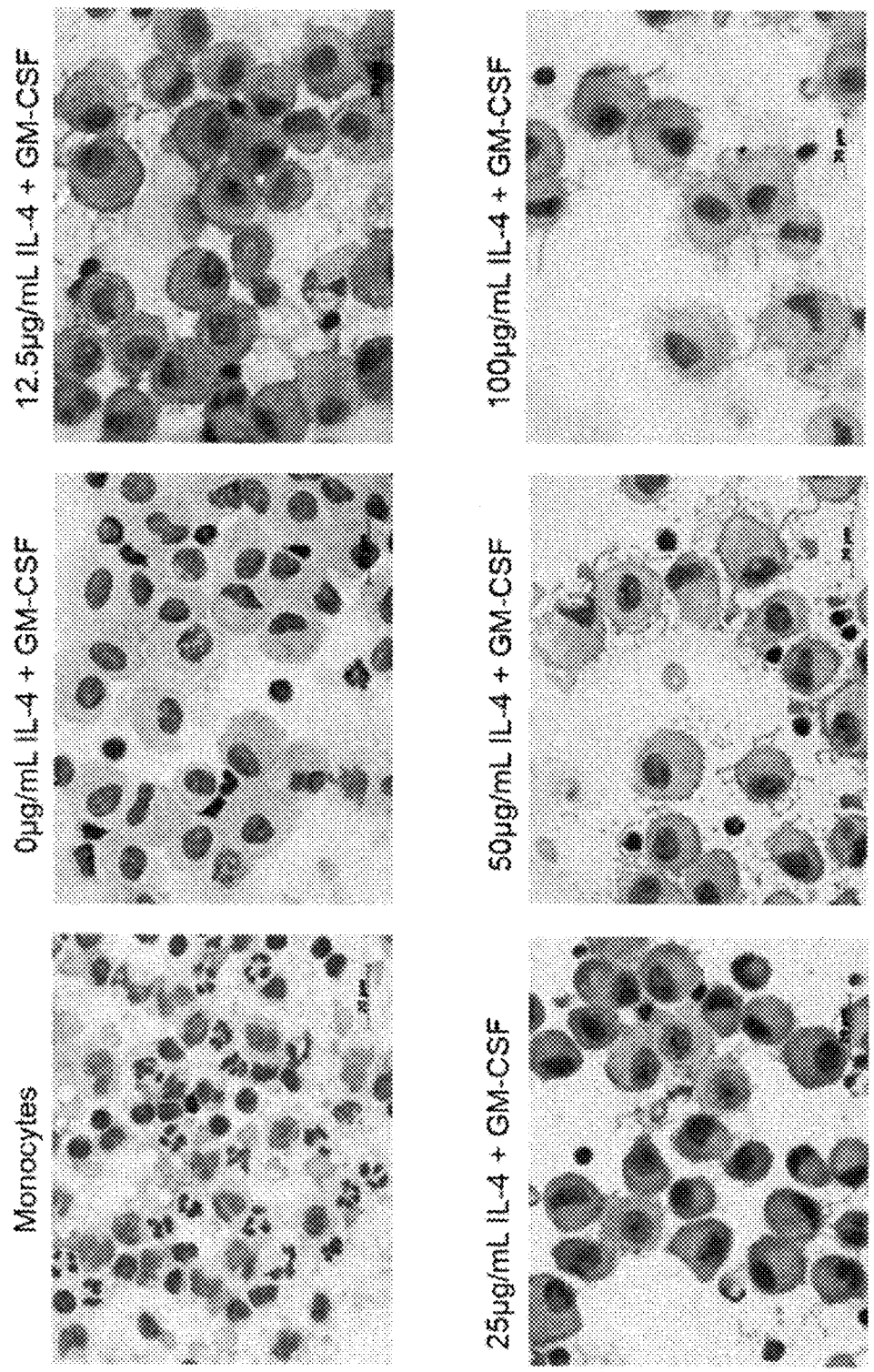
FIG. 1: Morphological visualization of immature dendritic cells differentiated from monocytes in the presence of different IL-4 and GM-CSF concentration. Monocytes were enriched from PBMCs and cultured in R-10 containing different concentrations of IL-4 and GM-CSF as indicated for 5 days at 37° C. Cells were then concentrated onto a coated cover slip using cytospin. The cells were permeabilized and then stained using a standard haematoxylin and eosin staining technique. The stained cells were visualized using a light microscope at 100× magnification (Nikon). The images are representative of samples from two individual donors.

Circulating dendritic cells commonly represent only a very small population (<1%) of circulating PBMCs. For the reason, it was decided to differentiate dendritic cells from monocytes by incubating the cells in the presence of CellGro® (CellGenix, USA) containing IL-4 and GM-CSF for 5 days at 37° C. in order to generate sufficient numbers of cells for experimental purposes. The immature dendritic cells were then phenotypically characterised using light microscopy (FIG. 1). In order to visualize differences in the morphology of cells cultured in the absence or presence of different concentrations of IL-4 and GM-CSF, the cells were stained using a standard haematoxylin and eosin (H & E) staining technique and visualised using a light microscope (Nikon). Cells cultured in the absence of IL-4 and GM-CSF were morphologically distinct when compared to cells cultured in the presence of 100 µg/mL IL-4 and GM-CSF (FIG. 1). The treated cells appeared larger in shape, but more importantly dendrites were visible on the exterior of the cells. A small proportion of cells cultured in the presence of 12.5, 25 and 50 µg/mL IL-4 and GM-CSF also expressed dendrites, but at a much lower frequency than that observed when the cells were cultured in the presence of 100 µg/mL IL-4 and GM-CSF (FIG. 1).

Optimisation of the Maturation Method to Generate Mature Dendritic Cells.

Figure 2:
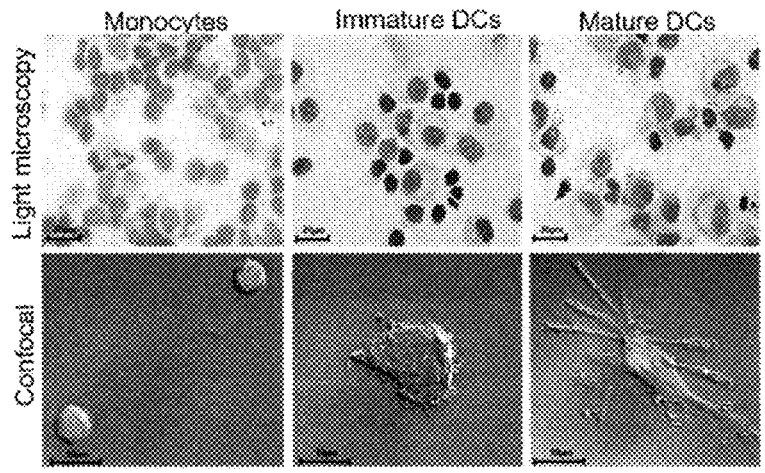
FIG. 2: Dendritic cells matured with Ampligen®, an IFN-containing cocktail and R848 express higher levels of co-stimulatory molecules compared to dendritic cells matured with Ampligen® and IL-1β or R848 and IL1-3.
Figure 2:
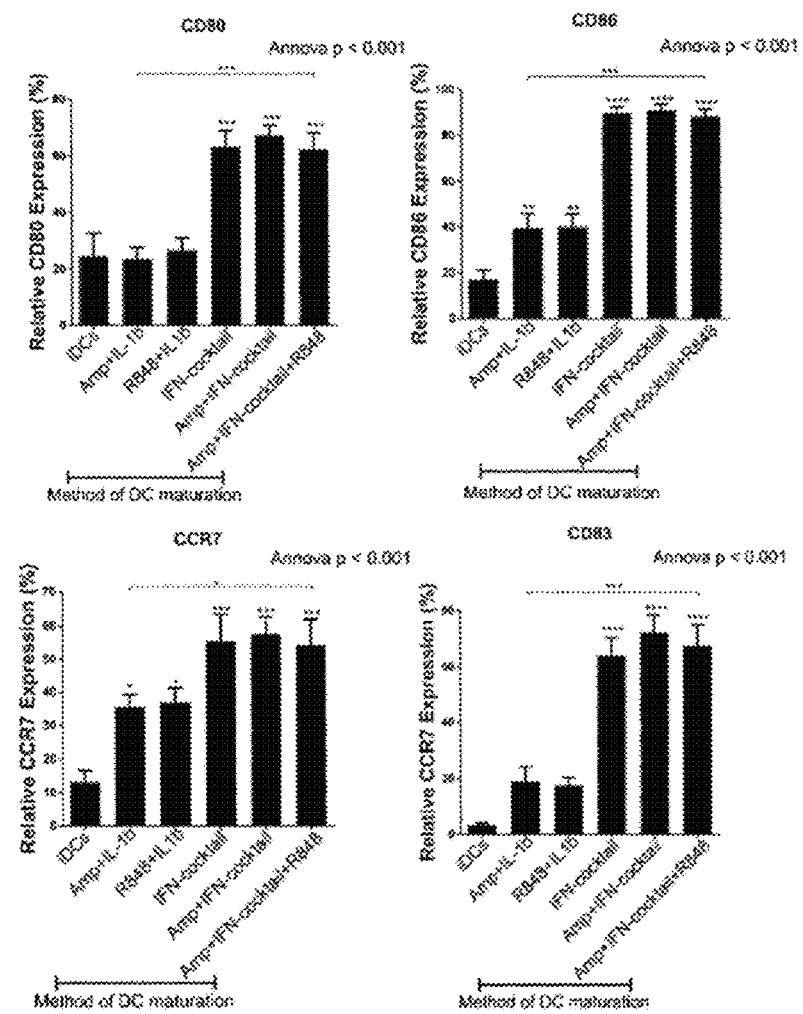

In order to determine if we could optimise the maturation phenotype of the dendritic cells ex vivo, we matured the dendritic cells with various combinations of Ampligen®, R848 or an interferon (IFN)-containing cocktail (IFN-α, IFN-γ, CD40L and IL-1β). The monocytes, immature dendritic cells and mature dendritic cells were morphologically distinct from one another (FIG. 2A). The immature and mature dendritic cells were larger than the monocytes and dendrites were clearly visible on the surface of the cells. The mature dendritic cells had more pronounced dendrites and were structurally different than the immature dendritic cells.

Next, we wanted to determine if the mature dendritic cells express high levels of the co-stimulatory molecules, CD80, CD86, CCR7 and CD83 using flow cytometry (FIG. 2B). The expression levels of both HLA-DR and CD40 increased above that observed with the IDCs for all the treatment conditions tested (data not shown). When the cells were matured with an IFN-containing cocktail in combination with Ampligen® a statistically significant increase in the key maturation markers CD86, CD80 and CD83 were observed above that with Ampligen® and IL-1β alone. The levels of CCR7 also increased significantly when the IFN-containing cocktail was included in maturation.

Determination of Whether Mature Dendritic Cells Produce IL-12p70 and IFN-γ, which are Important Predictors of how Well the Vaccine Will Perform In Vivo.

The ability of mature dendritic cells to produce biologically active IL-12p70 and IFN-γ Is a direct indicator of how clinically effective a dendritic cell vaccine can be, because it has the ability to activate effector T-cells in vivo, that have the potential to drive an anti-tumour response (Curtsinger et al. (1999), Schmidt and Mescher (1999), Xao Z et al. (2009)). For this reason, we wanted to determine the relative expression levels of IL12-p70 and IFN-γ from the mature dendritic cells using an IL12p70 ELISA and IFN-γ ELISPOT assays, respectively (FIG. 3).

The IDCs and non-matured dendritic cells produced no detectable IL12p70 however, in the presence of Ampligen®+IL-10 and R848+IL-1p, approximately 0.05 ng/mL to 0.15 ng/mL of IL12p70 was detected in the supernatants (FIG. 3A). A marked increase in IL12-p70 expression between 2 and 6 ng/mL was detected when the dendritic cells were matured with the IFN-containing cocktail alone or in combination with Ampligen® and/or R848. An approximate 40-fold increase in IL12p70 expression was detected in the presence of Ampligen®, an IFN-containing cocktail and R848 compared to Ampligen® and IL-1β alone (FIG. 3A).

In the presence of Ampligen® IL-1β and R848/IL-1β alone the mature dendritic cells produced approximately 500 SFU of IFN-γ per $10^6$ mature dendritic cells (FIG. 3B). However, in the presence of an IFN-containing cocktail only or in combination with Ampligen® and/or R848 an approximate 3 to 5-fold increase in IFN-γ was observed.

Example 2

Preclinical Trial Patients and Samples.

In the preclinical study 152 female patients with stage 1, 2 and 3 breast cancer were asked to consent to the study (FIG. 4). Twenty-five patients declined and 112 did not meet the inclusion criteria because they were on hormonal treatment, chemotherapy, HIV+, immunocompromised, had a genetic disorder or for personal reasons. Of the remaining 15 that were consented and recruited to the study a further 2 withdrew and 2 were excluded because they either did not disclose at the time of recruitment that they were on hormonal treatment or not enough biopsy material was obtained to complete the study. The remaining 11 female patients were included in the preclinical study.

The demographics of the study cohorts are shown in Table 1. The median age of the patients was 48 years. The patients were more likely to have non-invasive stage 2 breast cancer and the tumours expressed different breast cancer antigens including; estrogen receptor (ER), progesterone receptor (PR) and human epidermal growth receptor 2 (HER-2) as determined by immunohistochemistry (IHC). The primary breast cancer cells all expressed high levels of mucin-1 (MUC-1) and variable levels of the epithelial marker (epithelial cell adhesion molecule; Ep-CAM) and epithelial progenitor marker (integrin alpha 6; CD49f) as determined by flow cytometry. The breast cancer patients also expressed different HLA types (Table 1) and all had normal haemoglobin levels, white and red blood cell counts at the time of recruitment to the study (data not shown). The inventors HLA typed each patient, so that they could match them to the HER-2 and MUC-1 tetramers (HLA-A02) used in the study. The tetramer assay was used to show antigen presentation of MUC-1 and HER-2 on the mature dendritic cells and CD8+ T-cells. Therefore, the tetramer assay was only performed on those individuals that were HLA-02 positive.

Dendritic cells from breast cancer patients matured with Ampligen®, an IFN-containing cocktail and R848 or IFN-containing cocktail alone express high levels of key co-stimulatory molecules In order to obtain sufficient amounts of monocytes for the preclinical study each patient consented to a standard leukapheresis procedure using the Colbe Spectra Optia® Apheresis System. Following leukapheresis, the PBMCs were washed and the monocytes were isolated by plastic adherence. After differentiation into immature dendritic cells they were matured with or without 100 μg/mL tumour-specific lysate (lysate) for 6 hrs at 37° C. The cells were then matured with or without

TABLE 1

Demographic data of the cohorts used.

| Patient ID | Age | Stage | Invasive | Antigens expressed (IHC) ER | PR | HER-2 | Antigens Expressed (FC) Ep-CAM | CD49f | MUC-1 | HLA-type |
|---|---|---|---|---|---|---|---|---|---|---|
| PC001 | 44 | 3 | Yes | − | + | + | + | +++ | +++ | A30, A68 |
| PC003 | 58 | 2 | No | − | − | − | ++ | + | +++ | A02, A30 |
| PC004 | 71 | 3 | No | − | + | + | +++ | ++++ | +++ | A30, A33 |
| PC007 | 58 | 3 | No | − | + | + | ++ | +++ | +++ | A03, A11 |
| PC009 | 39 | 2 | No | + | + | + | + | ++ | +++ | A01, A03 |
| PC010 | 44 | 2 | No | + | + | + | + | + | +++ | A02, A66 |
| PC011 | 42 | 1 | No | + | + | + | ++ | + | +++ | A02, A24 |

TABLE 1-continued

Demographic data of the cohorts used.

| Patient ID | Age | Stage | Invasive | Antigens expressed (IHC) | | | Antigens Expressed (FC) | | | HLA-type |
| | | | | ER | PR | HER-2 | Ep-CAM | CD49f | MUC-1 | |
|---|---|---|---|---|---|---|---|---|---|---|
| PC012 | 48 | 2 | No | + | + | + | ND | ND | ND | A02, A11 |
| PC013 | 41 | 3 | Yes | − | − | + | +++ | ++ | +++ | A02 |
| PC015 | 38 | 2 | Yes | − | − | + | +++ | ++ | +++ | A02, A03 |
| PC016 | 44 | 3 | Yes | + | + | + | +++ | ++ | +++ | A02, A26 |

IHC = immunohistochemistry; FC = flow cytometry; HLA = human leukocyte antigen; + denotes 0-25% expression; ++ denotes 25-50% expression; +++ denotes 50-75% expression; ++++ denotes 75-100% expression; ND = not determined.

an IFN-cocktail only or Ampligen®, an IFN-containing cocktail and R848 for 42 hrs at 37° C. The maturation phenotype was determined by flow cytometry (FIG. 5). The dendritic cells that were matured with tumour-specific lysate only, an IFN-containing cocktail only or with Ampligen®, tumour-specific lysate, an IFN-containing cocktail and R848 expressed significantly higher levels of CD40 compared to IDC (data not shown).

More importantly, the dendritic cells matured with Ampligen®, tumour-specific lysate, an IFN-containing cocktail and R848 or IFN-containing cocktail alone, expressed significantly higher levels of the key maturation markers, CD80 (74%; p<0.05), CD86 (82%; p<0.005), CCR7 (50%; p<0.05) and CD83 (77%; p<0.005), compared to the iDCs (51% vs 6% vs 22% vs 1.8%, respectively) or dendritic cells matured with tumour-specific lysate alone (65% vs 14% vs 33% vs 7%, respectively; FIG. 5).

Mature Dendritic Cells from Breast Cancer Patients Produce High Levels of the Th1 Effector Cytokine IL-12p70.

The ability of mature dendritic cells to produce biologically active IL-12p70 is a direct indicator of how clinically effective a dendritic cell vaccine can be, because it has the ability to activate effector T-cells in vivo, that have the potential to drive an anti-tumour response (Curtsinger et al. (1999), Schmidt and Mescher (1999), Xiao Z et al. (2009)). IL-12p70 has been shown to be indispensable in regulating CD8+ effector function, T-cell activation and has been shown to be a key indicator in more favourable clinical outcomes amongst breast cancer patients (Curtsinger et al. (1999), Schmidt and Mescher (1999), Xiao Z et al. (2009), Kristensen et al. (2012)). The activation of IL-12p70 is regulated by TLRs and IFN-γ (Hayes et al. (1995), Mosca et al. (2000), Snijders at al. (1998)). For this reason, the inventors wanted to determine the relative expression levels of IL12-p70 from the supernatants of the mature dendritic cells using an IL12p70 ELISA (FIG. 6).

The immature dendritic cells or dendritic cells matured with the tumour-specific lysate only produced no detectable levels of IL-12p70 (FIG. 6). However, dendritic cells matured with the tumour-specific lysate, Ampligen®, an IFN cocktail and R848 expressed significantly higher levels (1.21 ng/ml, SD=0.3-3.7, p<0.005; FIG. 6) of IL-12p70. When the cells were matured with IFN-cocktail only the mean concentration of IL-12p70 was 0.6 ng/ml, which was significantly different to the cells that were matured with the tumour-specific lysate, Ampligen®, an IFN-containing cocktail and R848 (p<0.005).

T-Cell Receptors (TCRs) of CD8+ T-Cells Primed with Tumour-Specific Lysate Matured Dendritic Cells can Detect HER-2 and MUC-1 Antigens on MHC-1 Specific Tetramers.

The major histocompatability-1 complex (MHC-1)-specific tetramers were HLA-02 positive and as a result only matched patient samples were analysed for antigen presentation. Dendritic cells differentiated from monocytes and were matured with or without tumour-specific lysate for 6 hrs at 37° C. The cells were then matured with Ampligern, IFN-cocktail and R848 as indicated previously. The effector cells were generated by co-culturing PBMCs with the matured dendritic cells at a ratio of 1:10 (mature DC:PBMC) for 7 days at 37° C. Both HER-2 (4.5%; p<0.005) and MUC-1 (19%; p<0.05) tetramers were detected by the TCRs on CD8+ T-cells that were primed with the tumour-specific lysate matured dendritic cells (FIG. 7A). A 1.3 and 1.9-fold decrease in HER-2 (3%; p<0.05) and MUC-1 (11%) antigen recognition was observed by the TCRs of the CD8+ T-cells primed with dendritic cells matured in the absence of tumour-specific lysate.

Cytotoxic-T-Cell Mediated Cell Idlling of Primary Breast Cancer Cells with Ampligen®, IFN-Cocktail, R848 and Tumour-Specific Lysate-Matured Dendritic Cell Primed T-Lymphocytes.

The inventors wanted to determine if the mature dendritic cell-primed effector cell could elicit a T-lymphocyte-mediated cytotoxic response, which was tumoricidal to primary breast cancer cells in vitro. The effector cells were generated as indicated and cytotoxicity of the primary breast cancer cells were determined using the LDH assay (Cytotoxicity Detection KitPlus LDH; Roche, Germany; FIGS. 8A and B) and cell death of the primary breast cancer cells was measured by flow cytometry using the apoptosis detection kit from Becton Dickinson (FIGS. 8C and D).

When the PBMCs were primed with Ampligen®/IFN-cocktail/R848/tumour-specific lysate-matured dendritic cells, the median levels of breast cancer primary cell cytotoxicity was 75% (FIG. 8A; p<0.01) compared to primary cells incubated in the absence of effector cells. In contrast levels of cytotoxicity were 10%, 11% and 15%, when the PBMCs remained unprimed (PBMCs no dendritic cells) or were primed with tumour-specific lysate or IFN-containing cocktail only-matured dendritic cells, respectively. We also show that the levels of cytotoxicity observed when PBMCs were primed with Ampligen®/IFN-cocktail/R848/tumour-specific lysate-matured dendritic cells was dose-dependent (FIG. 8B).

Having shown that the PBMCs which were primed with Ampligen®/IFN-cocktail/R848/tumour lysate-matured dendritic cells could elicit a cytotoxic response to the primary breast cancer cells in vitro, we wanted to determine if these cells were tumoricidal in vitro. A 2-fold increase (p<0.05) in cytotoxic-mediated primary breast cancer cell kill was observed with effector cells that were primed with Ampligen®/IFN-cocktail/R848/tumour lysate-matured dendritic cells compared to primary cells not cultured with effector cells (FIG. 8C). We also observed a dose-dependent increase in the primary breast cancer cell kill when the PBMC were primed with Ampligen®/IFN-cocktail/R848/tumour lysate-matured dendritic cells (FIG. 8D).

Mature dendritic cells are sterile, endotoxin/mycoplasma free and cryopreservation does not affect their maturation phenotype or viability.

For the phase I/la clinical trial the vaccine will be administered over a 2-month period. For this reason, we wanted to determine if 2 months of cryopreservation affects the maturation phenotype or viability of the dendritic cells. As shown in Table 2, cryopreservation does not affect the maturation phenotype of the dendritic cells or viability. The expression levels of the co-stimulatory markers, CD80, CD86, CCR7 and CD83, remained at 84%, 86%, 68% and 77%, respectively. The mean viability was 74% and we show that all the vaccine preparations were sterile and endotoxin/mycoplasma free.

The present invention indicates that the inventors have optimally matured breast cancer patient-derived dendritic cells ex vivo with Ampligen®, IL-1β, IFN-γ, IFN-α, CD40L, R848 and tumour-specific lysate. These mature dendritic cells were able to present antigen and they had the ability to prime PBMCs, which resulted in Th1 cytotoxic T-lymphocyte-mediated killing of the patient's primary breast cancer cells in vitro. The inventors have further shown that the mature dendritic cells were sterile, endotoxin/mycoplasma free and they maintained their phenotype and high viability 2 months post-cryopreservation. No study has previously tested the efficacy of a dendritic cell vaccine using patient-derived primary cells in vitro.

TABLE 2

Expression of co-stimulatory molecules and viability of mature dendritic cells post 2 months of cryopreservation.

| Mean co-stimulatory molecule expression post cryopreservation (%) | | | | Mean viability (%) | GMP testing | | |
|---|---|---|---|---|---|---|---|
| CD80 | CD86 | CCR7 | CD83 | | Sterility (bacterial/mycology) | Endotoxins | Mycoplasma |
| 84 (70-90) | 86 (72-91) | 68 (53-70) | 77 (63-85) | 74 (60-84) | Yes | No | No |

Example 4

In Vitro Data Supporting the Efficacy of the Dendritic Cell Maturation Cocktail Using the Proposed Maturation Method Versus a Commercially Available Cocktail To prove the efficacy of the maturation method described herein, the maturation of the present invention was compared with the method disclosed in patent application number WO2014136845A1 consists of a cocktail that includes IFNγ, IFNα, CD40L and IL-1β. The patented cocktail does not contain the Toll-like receptor (TLR)-3 agonist, Ampligen® or the TLR-7 agonist, R848.

The immature dendritic cells were prepared as indicated in the patent specification. The immature dendritic cells were loaded with 100 µg/ml of MCF-7 lysate prepared as indicated in the methods of the main application. After 6 hrs incubation at 37° C., the cells were matured with an IFN-containing cocktail (25 ng/ml IFN-γ, 10 ng/ml IFN-α, 1 µg/mL CD40L and 10 ng/mL IL-1β; patent application number WO2014136845A1), or 100 µg/mL Ampligen®, and 2.5 µg/mL R848. After 42 hrs at 37° C. the supernatants were harvested and stored at −80° C. The levels of IL-12p70 were then determined using an IL-12p70 enzyme linked immunosorbent assay (ELISA) from Mabtech (USA) according to the manufacturer's instructions.

As expected very low levels of IL-12p70 were detected from the immature dendritic cells (FIG. 1). However, the levels of IL-12p70 detected from the dendritic cells matured with Ampligen®, an IFN-containing cocktail and R848 approached 2 ng/ml. The levels of IL12p70 observed from the dendritic cells matured with the maturation method described in patent application number WO2014136845A1 were 2.1-fold less than the method described in the present specification (FIG. 1; p<0.05). This data proves that the maturation method disclosed in this patent is far superior to any current patented maturation method. As a result, these dendritic cells would be expected to have very high efficacy in a clinical setting.

Example 5

Dendritic Cells from Healthy Volunteers can be Optimally Primed and Matured with Purified Protein Derivative, an IFN-Containing Cocktail and R848.

The PBMCs and immature dendritic cells were prepared as indicated previously. The cells were primed with purified protein derivative (PPD) for 6 hrs at 37° C., then matured with or without or in combination with an IFN-containing cocktail (10 ng/mL IFNα, 25 ng/mL IFNγ, 1 µg/mL CD40L and 10 ng/mL IL-1β), 100 µg/mL Ampligen® and/or 2.5 µg/mL R848 Ampligen® (referred to as full cocktail in combination) for 42 hrs at 37° C. (FIG. 10). The dendritic cells which were primed with 12 µg/ml purified protein derivative and matured with full cocktail or IFN-cocktail only expressed high levels of CD86 (87% [p<0.01] and 91% [p<0.005], respectively) and CD83 (76% and 84% [p<0.05]), respectively) compared to the immature dendritic cells (10.4% versus 24%; FIG. 10). The cells that remained un-primed/matured or were primed with purified protein derivative only expressed similar levels of CD86 (13.6% and 38.4% respectively) and CD83 (33% and 31%, respectively) to the immature dendritic cells.

Dendritic Cells Primed and Matured with Purified Protein Derivative and Full Cocktail Produce High Levels of the Key Th1 Effector Cytokine IL-12p70.

Having shown that we could optimally mature the dendritic cells with purified protein derivative and full cocktail we wanted to determine if these dendritic cells had the ability to produce high levels of IL12-p70. We show that the dendritic cells primed/matured with purified protein derivative and the full cocktail produced 0.32 ng/ml of IL-12p70 (FIG. 11). In contrast the levels produced from the dendritic cells matured with IFN-containing cocktail only were approximately 2-fold lower, however significance could not be established due to the small number of samples (n=3). The data presented here provides evidence that the vaccine would support a Th-1 immune response to TB, which has been shown to be important for regulating CD8+ effector function, T-cell activation and has been shown to be a key indicator in more favourable clinical outcomes amongst cancer patients.

Dendritic Cells Matured with Purified Protein Derivative and the Full Cocktail have the Ability to Prime Effector Cells Resulting in *Mycobacterium tuberculosis* Containment In Vitro.

Having shown that we could optimally mature the dendritic cells in vitro, which express high levels of the Th-1 effector cytokine, IL-12p70, we wanted to determine if the mature dendritic cells could prime effector cells resulting in increased *M. tuberculosis* containment in vitro. The effector cells that were primed with the purified protein derivative and full cocktail-matured dendritic cells increased effector-mediated containment 2-fold compared (p<0.05; FIG. 12) to effector cells that remained un-primed or were primed with purified protein derivative or IFN-containing cocktail-matured dendritic cells.

REFERENCES

1. Banchereau J, Steinman R M (1998) Dendritic cells and the control of immunity. Nature 392: 245-252.
2. Mellman I, Steinman R M (2001) Dendritic cells: specialized and regulated antigen processing machines. Cell 106: 255-258.
3. Curtsinger J M, Schmidt C S, Mondino A, Uns D C, Kedl R M, et al. (1999) Inflammatory cytokines provide a third signal for activation of naive CD4+ and CD8+ T cells. J Immunol 162: 3256-3262,
4. Schmidt C S, Mescher M F (1999) Adjuvant effect of IL-12: conversion of peptide antigen administration from tolerizing to immunizing for CD8+ T cells in vivo. J Immunol 163: 2561-2567.
5. XIao Z, Casey K A, Jameson S C, Curtsinger J M, Mescher M F (2009) Programming for CD8 T cell memory development requires IL-12 or type I IFN. J Immunol 182: 2786-2794.
6. Kristensen V N, Vaske C J, Ursini-Slegel J, Van Loo P, Nordgard S H, et al. (2012) Integrated molecular profiles of invasive breast tumours and ductal carcinoma in situ (DCIS) reveal differential vascular and interleukin signalling. Proc Natl Acad Sci USA 109: 2802-2807.
7. Hayes M P, Wang J, Norcross M A (1995) Regulation of interleukin-12 expression in human monocytes: selective priming by interferon-gamma of lipopolysaccharide-inducible p35 and p40 genes. Blood 86: 646-650.
8. Mosca P J, Hobeika A C, Clay T M, Nair S K, Thomas E K, et al. (2000) A subset of human monocyte-derived dendritic cells expresses high levels of interleukin-12 in response to combined CD40 ligand and interferon-gamma treatment. Blood 96: 3499-3504.
9. Snijders A, Kalinski P, Hilkens C M, Kapsenberg M L (1998) High-level IL-12 production by human dendritic cells requires two signals. Int Immunol 10: 1593-1598.

The invention claimed is:

1. A dendritic cell maturation cocktail consisting of a TLR-3 agonist, IFN-α, IFN-γ, CD40L, IL-1β, a TLR-7/8 agonist, and an antigen, wherein the antigen is a tumor-specific cell lysate or an infectious disease antigen, and wherein the TLR-3 agonist is a high molecular weight dsRNA polymer selected from the group consisting of poly [I]:poly [C12U] and poly [C]:poly [I12U].

2. The dendritic cell maturation cocktail of claim 1, wherein the TLR-7/8 agonist is R848.

3. The dendritic cell maturation cocktail of claim 1, wherein a dendritic cell matured with the dendritic cell maturation cocktail produces a higher level of IL-12p70 as compared to other dendritic cells matured with the maturation cocktail lacking the tumor-specific lysate or infectious disease antigens, the TLR-3 agonist, and the TLR-7/8 agonist.

4. A method of producing mature antigen-presenting dendritic cells in vitro, the method including the step of:
maturing an immature dendritic cell with the dendritic cell maturation cocktail of claim 1.

5. The method according to claim 4, wherein the immature dendritic cell is exposed to the dendritic cell maturation cocktail for sufficient time to induce the immature dendritic cell to capture and process the antigen.

6. A method of manufacturing a vaccine for inducing a cellular immune response in a subject, the method comprising the steps of:
maturing immature dendritic cells with the dendritic cell maturation cocktail of claim 1 until the immature dendritic cells become antigen-presenting mature dendritic cells; and
formulating the antigen-presenting mature dendritic cells in a pharmaceutically acceptable formulation.

7. The dendritic cell maturation cocktail of claim 1, wherein the high molecular weight dsRNA polymer is poly [I]:poly [C12U].

8. The dendritic cell maturation cocktail of claim 1, wherein the high molecular weight dsRNA polymer is poly [C]:poly [I12U].

9. The dendritic cell maturation cocktail of claim 1, wherein the antigen is a tumor-specific cell lysate.

10. The dendritic cell maturation cocktail of claim 1, wherein the antigen is an infectious disease antigen.

11. An in vitro method of producing mature dendritic cells, the method comprising the step of:
culturing immature dendritic cells in the presence of the dendritic cell maturation cocktail of claim 1.

12. The method of claim 11, wherein the TLR-7/8 agonist is R848.

13. The method of claim 11, wherein the immature dendritic cells are cultured from a sample of peripheral blood mononuclear cells.

14. The method of claim 13, wherein the sample is isolated from an animal.

* * * * *